United States Patent [19]
Hecht et al.

[11] Patent Number: 4,590,264
[45] Date of Patent: May 20, 1986

[54] LIPOGLYCOSIDES AND PROCESS OF EXTRACTING SAME

[75] Inventors: Sidney M. Hecht; David G. Lynn; Kalakota S. Reddy, all of Charlottesville, Va.

[73] Assignee: Wofor AG, Giswil, Switzerland

[21] Appl. No.: 522,270

[22] Filed: Aug. 11, 1983

Related U.S. Application Data

[63] Continuation-in-part of Ser. No. 467,767, Feb. 18, 1983, Pat. No. 4,454,124, which is a continuation of Ser. No. 280,078, Jul. 2, 1981, abandoned.

[51] Int. Cl.$^4$ ............................................. C07H 15/00
[52] U.S. Cl. .................................... 536/18.2; 536/4.1; 536/18.1; 536/128
[58] Field of Search ...................... 536/4.1, 18.1, 128, 536/18.2

[56] References Cited
U.S. PATENT DOCUMENTS 4,361,697  11/1982  Dobberstein et al. ............. 536/128
4,435,563  3/1984  Oepen et al. ..................... 536/128
4,454,124  6/1984  Hecht ................................ 424/195

OTHER PUBLICATIONS

Kupchan, "Cancer Treatment Reports", vol. 60, No. 8, Aug. 1976, pp. 1115–1126.

Primary Examiner—Johnnie R. Brown
Attorney, Agent, or Firm—Sherman and Shalloway

[57] ABSTRACT

This invention provides novel lipoglycosides having the structural formula:

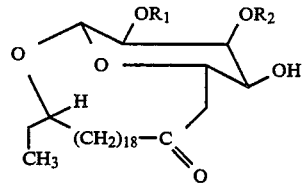

wherein $R_1$ and $R_2$ are different and are selected from the group consisting of hydrogen and

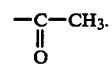

The lipoglycosides have antitumor properties.

6 Claims, No Drawings

LIPOGLYCOSIDES AND PROCESS OF EXTRACTING SAME

CROSS REFERENCE TO RELATED APPLICATIONS

This application is a continuation-in-part application of parent application Ser. No. 467,767, filed Feb. 18, 1983, issued on June 12, 1984 as U.S. Pat. No. 4,454,124, which is a continuation application of grandparent application Ser. No. 280,078, filed July 2, 1981, now abandoned.

BACKGROUND OF THE INVENTION

1. Field of the Invention

The present invention relates to novel compounds. More particularly, the present invention relates to novel lipoglycosides isolated from the plant *Cerastium viscusum* L. (Coryophyllaceae) Mississippi.

2. Description of the Prior Art

Crude extracts from plants have been used to treat diseases in humans for centuries. Recently, attempts have been made to extract and isolate pure tumor inhibiting compounds from plants. See, for example, S. M. Kupchan, "Novel plant-derived tumor inhibitors and their mechanisms of action," *Cancer Treat Rep* 60: 1115–1126 (1976). According to Kupchan, to obtain the desired extract, the plant is coarsely ground and subjected to extraction with a hot solvent in a Soxhlet apparatus. The temperature at which the extraction is conducted is substantially higher than room temperature but usually below 40° C. The solvents most often used in such an extraction process includes petroleum ether and methanol. The so-obtained crude extract is subjected to further processing (such as fractionation) to yield an extract of high purity.

In an alternative method, the plant may be extracted in a percolation apparatus with an acceptable solvent. This extraction method is also conducted at a temperature substantially higher than room temperature but usually below 40° C. The crude extract is also subjected to further processing to yield a product of higher purity.

As noted above, it is the normal procedure to extract plants using hot solvents. However, it is the present inventors' belief that extraction under heat is undesirable since some of the biologically active materials in the plant may be destroyed and lose its activity as a result of heating.

It has been known for several years that the species of Cerastium genus (Coryophyllaceae) are the source of flavoroid glycosides, fatty acids and the glycosides thereof. However, the activity of these glycosides against tumor cells has not been investigated as far as the present inventors are aware.

SUMMARY OF THE INVENTION

The present invention provides antitumor compounds isolated from the plant *Cerastium viscusum* L. (Coryophyllaceae) found in Mississippi. By subjecting the plant to sequential extraction at room temperature with several solvents and systematically fractionating the extracts by following the cytotoxicity of the extracts, novel lipoglycosides having the following structural formula have been obtained:

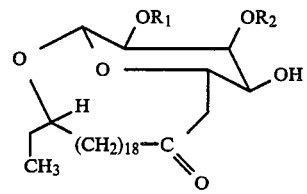

wherein $R_1$ and $R_2$ are different and are selected from the group consisting of hydrogen and

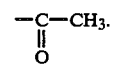

The lipoglycosides of this invention possess tumor-killing capabilities.

DETAILED DESCRIPTION OF THE INVENTION

According to the present invention, novel lipoglycosides having the structural formula

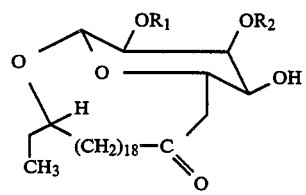

wherein $R_1$ and $R_2$ are different and are selected from the group consisting of hydrogen and $$-\overset{O}{\underset{\|}{C}}-CH_3,$$

have been isolated from the plant *Cerastium viscusum* L. (Coryophyllaceae) found in Mississippi. The plant is subjected to extraction in various solvents having different polarities (i.e. dielectric constants) at room temperature for a period of from 1 to 10 days. By room temperature, it is meant from about 20° C. to about 25° C. The extract-containing solvents are each tested for their biological activity. As a measure of biological activity, the cytotoxicity of the extracts against tumor cells derived from human carcinoma of the nasopharynx (KB cells) is measured. Those extracts which show the capability of killing KB cells are fractionated to yield the compounds of the present invention. To confirm the structures of the novel compounds, analytical methods and chemical reaction methods are used.

The bark, twig and wood portions of the plant are ground into small pieces. It is noted that the present plant is a tree of substantial size so that the season of collection of the plant should not have any effect on the chemical composition of the plant. The size to which the plant is ground is not critical since it only affects the length of the extraction period.

The ground plant is subjected to extraction in a series of solvents, each having a different polarity. The ground plant is completely submerged in a first solvent which is a hydrocarbon solvent having a dielectric constant at 20° C. to 25° C. within the range of from about 1.8 to about 2.0. Suitable solvents include pentane, hexane, heptane and petroleum ether with hexane being preferred.

Thereafter, the solvent is separated from the plant by any convenient method, i.e. decanting. The solvent containing the extract is evaporated to yield a residue. Since it is deemed undesirable to heat the solvent because heating may destroy some of the biologically active materials in the extract, a convenient method is to evaporate under a reduced pressure of from about 10 to about 100 mm Hg. The plant is then subjected to at least one additional extraction with fresh solvents. The products obtained from extractions with portions of the same solvent are pooled.

After extraction with the first solvent, the ground plant is extracted with the second, third and fourth solvents. The procedure used is identical to that described above. The second solvent has a dielectric constant ranging from about 3.5 to about 5.0 at 20° to 25° C. Examples thereof include methyl ether, ethyl ether, isopropyl ether and tetrahydrofuran, with ethyl ether being preferred. The third solvent has a dielectric constant ranging from about 15 to about 35 at 20° to 25° C. Useful examples thereof include methanol, ethanol, propanol, isopropanol and 1-butanol, with methanol being preferred. The fourth solvent is water which has a dielectric constant of about 78 at 25° C. From the above description, it can be seen that the solvent having the lowest dielectric constant (i.e. highest polarity) is used first, followed by a solvent having the next higher dielectric constant and so forth.

The extracts from each of the four solvents are tested for their anti-tumor activity by assaying with tumor cells derived from human carcinoma of the nasopharynx. For the present plant, the extracts from the second solvent, namely ethyl ether, have been found to possess antitumor activity. Hence, the ethyl ether extracts are subjected to further fractionation to isolate the active compound.

Since the ethyl ether extract has been found to contain the active fractions, it is preferred to extract the plant with ethyl ether only and to isolate the active compounds therefrom. Instead of ethyl ether, solvents having a dielectric constant at 20° to 25° C. of from about 3.5 to about 5.0 can be used. Examples of such solvents include methyl ether, ethyl ether, isopropyl ether and tetrahydrofuran.

The ethyl ether extract is concentrated under vacuum to produce a pale green residue which is partitioned between 10% aqueous methanol and n-hexane. Insoluble solid residues are filtered and tested for their activity. The aqueous methanol extract is concentrated under vacuum, with the so-obtained residue being partitioned between 20% aqueous methanol and carbon tetrachloride. The carbon tetrachloride layer is found to possess significant activity. The 20% aqueous methanol layer is concentrated and partitioned between carbon tetrachloride and 40% aqueous methanol. Both layers are concentrated and tested for activity. The carbon tetrachloride residue shows significant activity but the aqueous methanol residue is inactive.

The carbon tetrachloride extract from the 20% aqueous methanol partition is dissolved in a 1:1 (volume) mixture of methanol and carbon tetrachloride and fractionated by feeding to a silica gel column. The eluant used is a 1:1 solution of carbon tetrachloride and methanol. Sephadex LH 20, a hydroxypropylated derivative of a cross-linked product of dextran with epichlorohydrin, is a suitable silica gel. The fractions are tested for their activity against KB cells. The several active fractions are combined and evaporated to yield a residue. This residue is subjected to silica gel flash chromatography in methanol and carbon tetrachloride mixtures. The active fraction is purified by preparative high pressure liquid chromatography (HPLC). Two lipoglycosides having the structural formulae shown below are isolated.

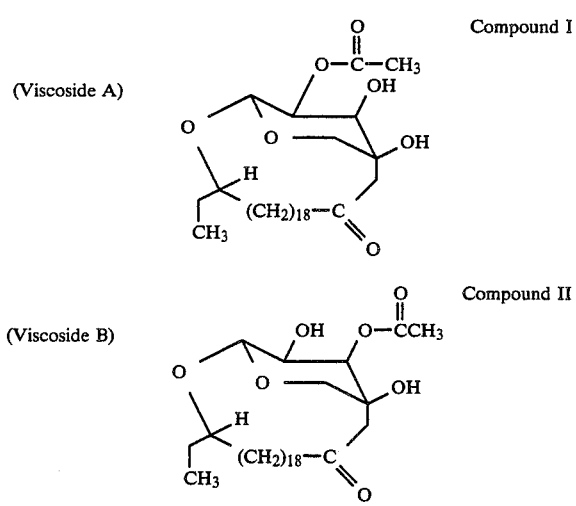

Properties of compound I
Colorless soft needles.
Melting point: 95°–100° C.
$R_f = 0.5$ (10% methanol in $CHCl_3$).
Soluble in $CHCl_3$, methanol.
Sparingly soluble in acetyl ethyl ether and acetone.
Insoluble in ethyl ether and petroleum ether.
$[\alpha]_D^{23} -18.6°$ ($CHCl_3$).
IR($CHCl_3$): 3300–3500 (br), 2920, 1740, 1710, 1460, 1370, 1280, 1080, 1030 and 790 cm$^{-1}$.
$^1$HMNR ($CDCl_3$): δ 0.85 (t,3) (J=7.0 Hz), 1.2–1.5 (br m, 38) 2.10 (s,3), 2.4 (m,2), 3.45 (br t,2), 3.56 (m,2), 4.35 (m,2), 4.5 (d,1) (J=8.9 Hz) and 4.72 (br t, 1).
$C_{30}H_{53}O_7$ (M—$H_2O$+1): Calculated: 525.3786; Found: 525.3782.
Mass spectrum: m/z 543[(M+H)$^+$, positive chemical ionization], 525 (M—$H_2O$+H), 483 (M—AeOH+H), 507, 465, 447, 429, 405, 379, 367, 339, 321, 247, 229, 205, 187, 169, 145, 127, 109, 97, 61.
$^{13}$CNMR (d-6 acetone): δ 173.12, 171.23, 102.31, 81.27, 81.20, 76.63, 75.27, 74.89, 72.07, 64.79, 36.25, 35.96, 35.48, 34.41, 33.00, 32.66, 31.79, 31.25, 31.01, 30.43, 30.23, 29.46, 28.87, 28.7, 27.95, 27.76, 27.18, 26.79, 23.68 and 14.75.
Properties of Compound II
Colorless viscous oil
Soluble in $CH_2Cl_2$, benzene
Insoluble in methanol, ethyl ether
UV end absorption
IR ($CHCl_3$): 3200–3500, 2890, 2940, 1750 (br), 1460, 1380, 1240, 1070, 1050, 890,720 cm$^{-1}$.
$^1$HNMR ($CDCl_3$): δ 0.9 (t,3) (J=7 Hz), 1.15–140 (br m,32) 1.70 (br t,4) 2.12 (s,3), 2.35 (m,2), 3.4 (t,1) (J=9 Hz), 3.45 (t,1) (J=9 Hz), 3.60 (t,1) (J=9.0 Hz), 3.65 (m,1) 4.05 (dd,1) (J=12.6, 7.2 Hz), 4.50 (d,1)(J=8.2 Hz), 4.65 (dd 1) (J=12.6;2.5), 4.70 (t,1) (J=9.0 Hz)
$^{13}$CNMR ($CDCl_3$): δ173.79, 171.16, 101.93, 76.37, 77.20, 76.75, 74.28, 74.15, 63.98, 34.20, 34,32.5, 31.89, 29.65, 29.49, 29.33, 27.70, 26.86, 26.82, 26.62, 26.54, 25.04, 24.25, 24.19, 22.65, 20.95 and 14.07.

$C_{30}H_{53}O_7(M-H_2O+H)^+$: Calculated: 525.3782. Found: 525.3786.

Mass spectrum: 543 [$(M+H)^+$ positive chemical ionization] 525. ($M-H_2O$), 507,493, 475, 447, 429, 411, 395, 379, 349, 339, 321, 285, 257, 247, 229, 205 (M-aglycone), 187, 169, 155, 145, 127, 115, 109, 97, 81, 61.

To confirm the structures of compounds I and II, chemical interconversion methods are used. The results and methods of testing are described in the examples.

As stated above, compounds I and II which have been isolated from *Cerastium viscusum* possess antitumor properties as indicated by their activity against tumor cells derived from human carcinoma of the nasopharynx (KB cells).

The following examples further illustrate the present invention. These examples should not be construed to be restrictive as they merely illustrate the present invention.

EXAMPLES

I. Apparatus Used

Melting points were measured on a Thomas Hoover Capillary Melting Point Apparatus and are uncorrected. Preliminary fractionation was carried out with Sephadex LD-20, particle size 25–100μ. Column chromatography was carried out with Silica gel 60, particle size 0.063–0.200 mm, Merck. Thin layer chromatography (TLC) monitoring of all reactions was performed with Merck silica gel 60 F254 precoated sheets (0.2 mm) and preparative TLC separations were carried out on 20×20 cm glass plates coated with Merck G.F.−254 silica gel and developed with 5% methanol-CHCl₃, or as indicated. Paper chromatography was performed on Whatman No. 1 paper, development with n-butanol-EtOH-H₂O (5:1:4). Chromatograms were visualized with aniline hydrogen phthalate spray, heated at 100° C. for 15 min. Flash column chromatography was carried out using Merck silica gel, particle size 0.40–0.062 mn, 230–400 mesh. TLC spots were visualized with Ce($SO_4$)₂ (5%) solution. High pressure liquid chromatography was performed on a Waters Associates instrument with a Refeactive Index detector. A Whatman partisil M9 10/50 column was employed for separations; the solvent was 2% methanol in CHCl₃. UV spectra were measured with a Cary 15 spectrophotometer; IR spectra with a Perkin Elmer 257 Grating spectrophotometer. ¹H-NMR spectra were obtained on JOEL FX-100 or Nicolet NT 360 spectrometers. All values are reported as ppm downfield from Me₄Si. ¹³C-NMR were obtained on a JEOL, JNM-PFT-100 spectrometer operating at 25.15 MHz in the Fourier transform mode. Spectral widths of 500 Hz and the use of 8K data points resulted in acquisition times and pulse delays of 0.8 seconds. The pulse widths used correspond to flip angles of 42°–45° with a repetition rate of 1–2 sec. Spectra were taken at probe temperature 23°±2° C. All the reported ¹³C chemical shifts are in ppm downfield from internal TMS, for solutions in CDCl₃.

Electron-impact mass spectral data was obtained with a Hitachi RMU-6E, chemical ionization high-resolution mass spectral data with an AEI-MS 902 modified for chemcial ionization.

II. KB Cell Assay

A sample of cells was taken from a stock supply furnished by a well known commercial laboratory. The primary culture was Minimal Essential Medium (MEM), Flo Laboratories, 10% fetal calf serum. Trypsinization was conducted with 0.2% trypsin in isotonic NaCl. The cells were counted with 0.1% Tripan Blue. The cells were subcultured in a 5 to 1 split in microtiter plates at $2 \times 10^5$ cells per well. The volume of culture placed in each well was 1 ml. The cells were counted at three locations before the addition of the extract to yield an average cell count.

Each of the extracts to be tested was added to the cells at a specific concentration as an ethanolic solution. The cells were incubated at 37° C. for 48 hours. Thereafter, the cells were again counted at three locations to provide an average cell count.

As a control, a cell sample was incubated for the same period in culture medium and without the addition of any plant extract. It was found that after incubation the concentration of the cell was usually doubled, indicating viable cell growth.

EXAMPLE 1

Three-hundred (300) gm of the ground twigs of *Cerastium viscusum* L. (Coryophyllaceae) Mississippi were extracted at room temperature with 1.5 liters of hexane. This extraction step was repeated once to yield a total of 3.16 gm extract. The twigs were rinsed twice with hexane and dried in a laboratory hood.

The twigs were then extracted at room temperature with 1.5 liters of ethyl ether. This extraction step is repeated twice to yield a total of 2.0 gm extract. The twigs were then rinsed with ether and dried in a hodd.

The twigs were thereafter extracted at room temperature with 1.5 liters of methanol. This extraction step was repeated twice to yield a total of 12.32 gm extract. The twigs were rinsed twice with methanol and dried in a hood.

The twigs were then extracted with 1.5 liters of water. This extraction step was repeated twice to yield a total of 16.84 gm extract.

Each of the extracts obtained above was tested for its effect on KB cells. The cell culture assay protocol described above was used.

The results obtained are presented in Table 1.

EXAMPLE 2

Example 1 was repeated with 600 g of ground twigs, using hexane and ether as solvents. The results are also shown in Table 1.

TABLE 1

| | | | | | Cell count after incubation | | | |
|---|---|---|---|---|---|---|---|---|
| | | | Volume | Total | KB | | KB | |
| | | Extraction | of solvent | wt. of extract | (100 μg/ml) | | (10 μg/ml) | |
| | Solvent | cycles | liters | gm | alive | dead | alive | dead |
| Example 1 | Hexane | 2 | 1.5 | 3.16 | 98 | 8 | 198 | 6 |
| | Ether | 3 | 1.5 | 2.0 | 1 | 110 | 200 | 1 |
| | Methanol | 3 | 1.5 | 12.32 | 177 | 7 | | |

Cell count before incubation 100

TABLE 1-continued

| | | | Volume of solvent liters | Total wt. of extract gm | Cell count after incubation | | | |
|---|---|---|---|---|---|---|---|---|
| | | | | | KB (100 μg/ml) | | KB (10 μg/ml) | |
| | Solvent | Extraction cycles | | | alive | dead | alive | dead |
| | Water | 3 | 1.5 | 16.84 | 133 | 9 | | |
| Example 2 | Hexane | 3 | 3.0 | | 0 | 70 | 300 | 20 |
| | Ether | 3 | 3.0 | | 0 | 60 | 240 | 9 |
| Control | | | | | 200 | 4 | 220 | 8 |

EXAMPLE 3

This example illustrates the procedure whereby the active compounds in the ethyl ether extract obtained in Examples 1 and 2 are isolated and identified.

Two gm of the ether extract obtained in Examples 1 and 2 were concentrated under vacuum to yield a pale green residue which was partitioned between 100 ml of 10% aqueous methanol and n-hexane. The insoluble solid (0.1 g) was filtered off and tested for its activity against KB cells. None was found. Neither was activity found in the n-hexane fraction ( 0.53 g).

The aqueous methanol fraction was concentrated under vacuum to obtain a residue (1.37 g.) which was in turn partitioned between 100 ml of 20% aqueous methanol and carbon tetrachloride. The carbon tetrachloride layer was concentrated (0.91 gm) and tested for its activity against KB cells. The results are shown in Table 2.

TABLE 2

| Cell count before incubation = 100 | | |
|---|---|---|
| Concentration of extract, μg/ml | Cell count after incubation | |
| | alive | dead |
| 10 | 200 | 8 |
| 50 | 3 | 115 |
| 100 | 0 | 140 |
| 0 (control) | 200 | 0 |

The carbon tetrachloride residue (0.91 gm) obtained above was dissolved in a 1:1 solution of methanol and chloroform. The solution was fractionated by feeding to a column (113.5×2.25 cm) containing Sephadex LH 20 using a methanol:chloroform (1:1) solution as the eluant. The fractions were tested for their activity against KB cells, with the active fractions being combined. A residue of 67.5 mg was obtained. This residue was subjected to silica gel flash chromatography (silica gel, 2.1 g) using a 1.5% methanol in chloroform solution as eluant. One active fraction (18.5 mg) was obtained and was further purified by preparative high pressure liquid chromatography using a 2% methanol in chloroform solution as eluant. Two active compounds I and II were so isolated, as shown in Table 3. Compound I comprises colorless soft needles having a melting point of 95°-100° C. whereas Compound II is a colorless viscous oil, soluble in $CH_2Cl_2$ and benzene but insoluble in methanol and ether.

TABLE 3

| Cell count before incubation = 100 | | |
|---|---|---|
| | Concentration of extract, μg/ml | Cell count after incubation |
| | | alive dead |
| Compound I | 10 | 15  0 |

TABLE 3-continued

| Cell count before incubation = 100 | | | |
|---|---|---|---|
| | Concentration of extract, μg/ml | Cell count after incubation | |
| | | alive | dead |
| | 100 | 0 | 0 |
| Compound II | 10 | 104.5 | 0.5 |
| | 100 | 0 | 0 |
| Control | 0 | 200 | 0 |

The following examples illustrate experiments conducted to confirm via chemical interconversions the structures of Compounds I and II.

EXAMPLE 4

Conversion of Compound I to its triacetate

Five mg (0.01 mmol) of Compound I was converted to its triacetate by treating with 0.2 ml of dry pyridine and 0.2 ml of acetic anhydride at 25° C. for 12 hours. The resulting mixture was poured into 10 g. of crushed ice. The product was extracted into 5 ml of methylene chloride three times. The methylene chloride extract was washed successively with 1N HCl, saturated sodium bicarbonate solution and water. Thereafter, it was dried over anhydrous sodium sulfate. After concentration, a colorless gummy solid (5 mg) was obtained. $R_f=0.7$ (5% $CH_2Cl_2$ in methanol). NMR ($CDCl_3$): δ 0.87 (t,3) (J=7 Hz), 1.2-1.4 (brm, 34), 1.6 (m,2), 1.95 (s,3), 2.01 (s,3), 2.07 (s,3) 2.30 (m,2) 3.55 (m,1), 3.65 (brm,1), 4.12 (brd,1) 4.20 (m,1), 4.55 (d,1) (J=9 Hz), 4.97 (t,1) (J=9 Hz), 5.02 (t,1) (J=9 Hz), 5.20 (t,1) (J=9 Hz). Mass spectrum: 626 ($M^+$,EI), 566 (M−Acetic acid), 506 (M−2 acetic acid), 485, 460,456, 446 (M−3xacetic acid) 492, 421, 400, 363, 321, 294, 289, 263, 253, 239, 225, 197, 183 and 169.

EXAMPLE 5

Acid hydrolysis of Compound I

Five mg (0.01 mmol) of Compound I purified by high pressure liquid chromatography was heated at 90° C. in 3.0 ml of 50% aqueous methanol containing 5% concentrated sulfuric acid for 12 hours. Thereafter, the reaction mixture was diluted with 10 ml of water. The deposited precipitates were extracted with 6 ml chloroform three times and the extracts washed with 10 ml of water. The extracts were dried to yield 2.5 mg of a white waxy solid product having a melting point of about 45° C. and $R_f=0.92$ (15% methanol in $CHCl_3$. The solid product was resistant towards crystallization from various organic solvents. The product is soluble in n-hexane, benzene and chloroform but insoluble in methanol and acetone. NMR ($CDCl_3$): δ 0.8 (t,3) (J:72 Hz) 1.2 (m,20), 1.35 (m,8), 1.55 (brt,10); 2.10 (t,2) (J=7.2 Hz) 3.52 (m,1), 3.6 (s,3). $^{13}CNMR$ $d_6$-benzene): δ 171.71, 71.73. (CH—OH), 45.86 (—O$\underline{C}H_3$), 39.16, 38.19, 34.16, 32.37, 31.79, 30.19, 20.85, 29.51, 26.20, 26.16, 25.33, 23.15, 14.36. $C_{23}H_{45}O_2(M-H_2O+H)^+$: calculated 353.3422; found 353.3419.

Mass spectrum: m/z 369[$(M-H)^-$, negative chemical ionization] 353,337, $C_{22}H_{40}O$(M−Sugar, Calculated 320.3082, found 320.3079), 229.1804, 200.1776, 185, 179, 171, 153, 143, 139, 129, 125, 115, 111, 97, 83 and 71.

From the spectral data the structure of the hydrolized product was tentatively established as 20-hydroxydocosanoic acid methyl ester.

The combined aqueous phase of the hydrolysate was heated at 90° C. for one hour, cooled and neutralized with saturated solution of $BaCO_3$. The precipitated $BaSO_4$ was filtered. The filtrate was concentrated and the residue so obtained was tested for carbohydrates. only glucose [$R_f$=0.23; development with 5:1:4 n butyl alcohol-acetic acid-water] was identified by paper chromatography by comparing with an authentic sample.

EXAMPLE 6

20-O-acetyldocosanoic acid methyl ester

The product of Example 5 (3 mg, 0.008 mmol) was converted to its monoacetate by treatment with 0.2 ml of dry pyridine and 0.2 ml of acetic anhydride at 25° C. for 12 hours. The reaction mixture was diluted with toluene (5 ml) and evaporated under vacuo. The residual pyridine and acetic anhydride were removed by co-distillation with toluene and the residue was purified by silica gel chromatography using chloroform as the eluant. The product obtained was a colorless semisolid.

NMR ($CDCl_3$): δ 0.88 (t,3), (J=7.2 Hz), 1.2–1.37 (m,28), 1.5 (m,4), 1.65 (m,4) 2.05 (s,3), 2.3 (t,2) (J=7.2 Hz), 3.65 (s,3), 4.85 (m,1).

Mass spectrum: m/z 413[$(M+H)^+$ positive chemical ionization], 353 (M−acetic acid), 271, 257, 243, 229, 215, 172 and 91, 57.

EXAMPLE 7

Base hydrolysis of Compound I

Five mg of Compound I (0.01 mmol) was dissolved in 0.5 ml of methanol and treated with five drops of 0.5N methanolic NaOH solution at room temperature for 24 hours. The reaction mixture was neutralized with glacial acetic acid, adjusted to a pH of 7 and concentrated under vaccum. The resulting residue was partitioned between chloroform and water (5 ml each) three times. The organic phase was thoroughly washed with distilled water (three times, 5 ml), dried over sodium sulfate and then concentrated under vacuum to yield 2.5 mg of colorless oily product which was purified by silica gel column chromatography using chloroform as eluant. $R_f$=0.3 (5% methanol in chloroform). $^1$HNMR ($CDCl_3$): δ 0.8 (t,3) (J=7.2 Hz), 1.1–1.35 (brm, 28), 1.45 (m,4), 1.5–1.6 (m,4), 2.25 (t,2) (J=7.2 Hz), 3.25 (m,2), 3.5 (m,2) 3.60 (s,3), 3.77 (brdd,2), 4.25 (d,1) (J=7.2 Hz).

EXAMPLE 8

Acetylation of product of Example 7

2.5 mg of the product of Example 7 (0.0048 mmol) was treated with 0.1 ml of dry pyridine and 0.1 ml of acetic anhydride at room temperature for 12 hours. The reaction mixture was diluted with distilled toluene and concentrated under vacuum to dryness. The residual pyridine was co-distilled with toluene. The resulting residue was purified by silica gel preparative thin layer chromatography in 5% methanol in chloroform. A colorless gum was obtained (2.5 mg). $R_f$=0.75 (5% methanol in chloroform. $^1$HNMR ($CDCl_3$): δ 0.9 (t,3), 1.2–1.4 (m,28), 1.45 (m,4), 1.65 (m,4), 2.0 (s,3), 2.05 (s,6), 2.07 (s,3), 2.35 (t,2) (J=7.2 Hz), 3.52 (q,1), 3.67 (m,1) 4.12 (dd,1) (J=12.6,2.5 Hz), 4.22 (dd,1) (J=5.4, 12.6 Hz), 4.52 (d,1) (J=8.0 Hz), 4.9 (t,1) (J=9 Hz), 5.05 (t,1) (J=9 Hz), 5.20 (t,1) (J=9 Hz).

EXAMPLE 9

Conversion of Compound II to its acetate 5.0 mg (0.01 mmol) of Compound II was converted to its acetate by treating with 0.2 ml of pyridine and 0.2 ml of acetic anhydride at room temperature for 12 hours. The reaction mixture was evaporated under vacuum and the residue was partitioned between chloroform and water. The chloroform extract was dried over sodium sulfate and concentrated under vacuum to yield 5 mg of the triacetate. Through co-thin layer chromatography and nuclear magnetic resonance spectroscope analyses, this triacetate was determined to be identical to the product obtained in Example 4 which is the triacetate of Compound I. $^1$HNMR ($CDCl_3$):δ 0.87 (t,3) (J=7.2 Hz), 1.2–1.4 (brm, 28), 1.5–1.65 (m,4), 2.0 (s,3), 2.02 (s,3), 2.05 (s,3), 2.30 (m,2), 3.60 (m,1), 3.70 (m,1), 4.32 (dd,1) (J=12.6, 2.0 Hz), 3.92 (dd,1) (J=12.6, 7.2 Hz), 4.55 (d,1)(J=8.9 Hz), 4.92 (overlapped t,2) (J=9 Hz), 5.22 (t,1) (J=9 Hz). $^{13}$CNMR(d-6 acetone): 175.60, 173.70, 175.40, 170.36, 99.30, 76.63, 76.29, 75.95, 17.13, 72.56.

Mass spectrum: 626 ($M^+$,EI), 556 (M AcOH), 506 (M−2×AcOH), 485, 460, 456, 446(M−3×AcOH), 429,421, 400, 363, 321(M−sugar), 294, 289, 253, 239, 225, 197, 183, 169.

EXAMPLE 10

Acid Hydrolysis of Compound II

Five mg. (0.01 mmol) of Compound II was treated with 3 ml of 50% aqueous methanol containing 5% concentrated sulfuric acid at a refluxing temperature for 7 hours. The reaction mixture was cooled, diluted with 5 ml of water. The precipitated product was filtered, washed with 2 ml of water three times and dried. The solid was purified by feeding it through a 1 g. column of silica gel using chloroform as the eluant. The product (2.5 mg.) obtained was a waxy solid. Through co-thin layer chromatography and nuclear magnetic resonance spectroscopic analyses, the product was identified to be the same as that obtained in Example 5.

$^1$HNMR($CDCl_3$): δ 0.85 (t,3) (J=7.2 Hz), 1.2–1.35 (brxm) 1.4–1.5 (m,2) 1.6 (brt,2), 2.3 (t,2) (J=7.2 Hz). 3.60 (m,1) and 3.65 (s,3).

This product also yielded a monoacetate upon treatment with pyridine-acetic anhydride at room temperature. This monoacetate was found to be identical to the monoacetate obtained from Compound I through co-thin layer chromatography, nuclear magnetic resonance and mass spectra.

The aqueous phase of the hydrolysate was heated at 90° C. for one hour, cooled, neutralized with barium carbonate solution and tested for carbohydrates. Only β-glucose[$R_f$=0.2, development with 5:1:4 n butanol:acetic acid:water] was identified by paper chromatography and comparison with an authentic sample.

EXAMPLE 11

Base Hydrolysis of Compound II

Four mg (0.007 mmol) of Compound II was treated with 2 ml of methanol and 4 drops of 0.5N methanolic NaOH solution at room temperature under a nitrogen atmosphere for 12 hours. The reaction mixture was neutralized with glacial acetic acid and the resulting solution concentrated under vacuum to dryness. The residue was partitioned between chloroform and water. The chloroform fraction was washed with water, dried over sodium sulfate and concentrated under vacuum. The product (2.8 mg) obtained was a colorless gum which was purified by thin layer chromatography, with 5% methanol in chloroform as the eluant. $^1$HNMR(CDCl$_3$): δ 0.85 (t,3) (J=7.2 Hz), 1.1–1.35 (brm, 36), 1.4–1.45 (m,2), 1.55–1.65 (brm, 4), 2.25 (t,2) (J=7.2 Hz), 3.27 (m,1), 3.45–3.59 (m,2), 3.60 (s,3),3s(brdd,2), 4.25 (d,1) (J=8.1 Hz). This product was converted to its tetraacetate by treatment with 0.2 ml of pyridine and 0.2 ml of acetic anhydride at room temperature for 12 hours. After extractive work up, 2.8 mg of a product, a colorless semisolid, was obtained. $^1$HNMR (CDCl$_3$): δ 0.9 (t,3) (J=7.2 Hz); 1.1–1.39 (brm, 32), 1.45 (brd,2), 1.64 (brt, 4) (J=9 Hz), 2.0 (s,3), 2.05 (s,6), 2.10 (s,3), 2.32 (t,2) (J=7.2 Hz), 3.55 (quintet, 1), 3.67 (s,3) (m,1), 4.13 (dd,1)(J=10.8, 3.6 Hz), 4.23 (dd,1) (J=5.4, 10.8 Hz), 4.54 (t,1) (J=9.0 Hz), 4.98 (t,1) (J=9.0 Hz), 5.07 (t,1) (J=9.0 Hz), 5.21 (t,1) (J=9.0 Hz). Mass spectrum=m/e 331 (peracetylated hexose) (M-aglycone, chemical ionization), 369 (M−sugar), 353 (M−sugar−methanol +H), 289, 271, 271, 257, 229, 211 and 169 and 109. Through NMR and Co thin layer chromatography analyses, this compound was determined to be identical to the product of Example 8.

The following is a flow chart of the chemical interconversions conducted in Examples 4–10.

(A) Acid hydrolysis

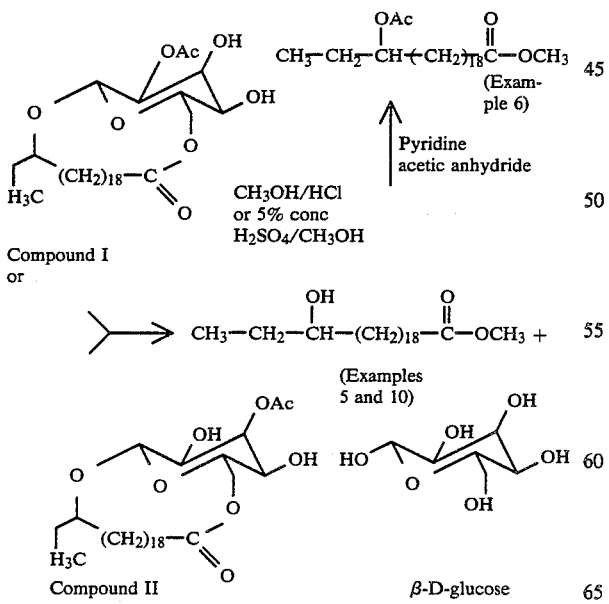

(B) Base hydrolysis

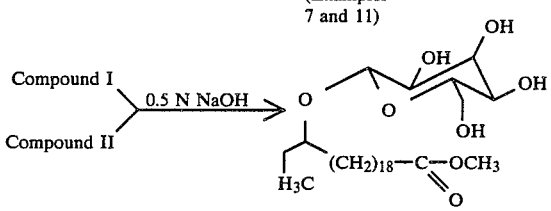

(Examples 7 and 11)

pyridine acetic anhydride
(Examples 8 and 11)

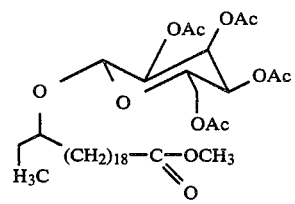

(C) Conversion to triacetate

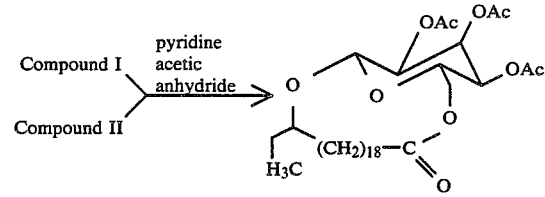

(Examples 4 and 9)

What is claimed is:
1. A compound having the formula:

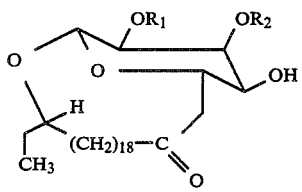

wherein R$_1$ and R$_2$ are different and are selected from the group consisting of hydrogen and

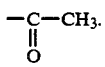

2. The compound of claim 1 wherein R$_1$ is hydrogen and R$_2$ is

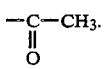

3. The compound of claim 1 wherein R$_1$ is

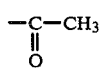

and R$_2$ is hydrogen.

4. A method of isolating the compounds of claim 1 from the plant *Cerastium viscusum* L. (Coryophyllaceae) found in Mississippi comprising:
(a) extracting the plant at room temperature with a solvent having a dielectric constant at 20° C. to 25° C. of from about 3.5 to about 5.0;
(b) partitioning the extract in a solution of 10% aqueous methanol and n-hexane;
(c) collecting the residue in the aqueous methanol fraction;
(d) partitioning the residue of (c) between 20% aqueous methanol and carbon tetrachloride;
(e) collecting the residue in the carbon tetrachloride fraction;
(f) fractionating the residue of (e) and collecting the active fractions capable of killing tumor cells derived from human carcinoma of the nasopharynx.

5. The method of claim 4 wherein the solvent in step (a) is selected from the group consisting of methyl ether, ethyl ether, isopropyl ether and tetrahydrofuran.

6. The method of claim 4 which further comprises (g) subjecting the active fraction from step (f) to silica gel flash chromatography in a mixture of methanol and carbon tetrachloride,
(h) collecting the active fraction from step (g), and
(i) subjecting the active fraction from (h) to high pressure liquid chromatography and isolating thereby the lipoglycoside compounds of formula

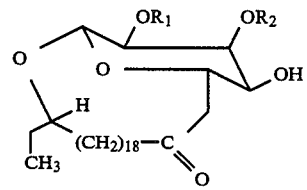

wherein $R_1$ and $R_2$ are different and are H or

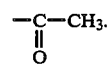

* * * * *